(12) United States Patent
Cole

(10) Patent No.: US 10,602,944 B2
(45) Date of Patent: Mar. 31, 2020

(54) DETECTING ARTIFACTS IN A SIGNAL

(71) Applicant: Draeger Medical Systems, Inc., Andover, MA (US)

(72) Inventor: Bryan Thomas Cole, Marlborough, MA (US)

(73) Assignee: DRÄGERWERK AG & CO. KGAA, Lübeck (DE)

( * ) Notice: Subject to any disclaimer, the term of this patent is extended or adjusted under 35 U.S.C. 154(b) by 592 days.

(21) Appl. No.: 15/303,490

(22) PCT Filed: May 6, 2015

(86) PCT No.: PCT/US2015/029521
§ 371 (c)(1),
(2) Date: Oct. 11, 2016

(87) PCT Pub. No.: WO2015/171804
PCT Pub. Date: Nov. 12, 2015

(65) Prior Publication Data
US 2017/0027464 A1    Feb. 2, 2017

Related U.S. Application Data

(60) Provisional application No. 61/990,180, filed on May 8, 2014.

(51) Int. Cl.
*A61B 5/04*      (2006.01)
*A61B 5/0452*    (2006.01)
*A61B 5/00*      (2006.01)

(52) U.S. Cl.
CPC ...... *A61B 5/04017* (2013.01); *A61B 5/04014* (2013.01); *A61B 5/0452* (2013.01);
(Continued)

(58) Field of Classification Search
CPC . A61B 5/04017; A61B 5/0456; A61B 5/7207; A61B 5/7264
(Continued)

(56) References Cited

U.S. PATENT DOCUMENTS 3,768,093 A * 10/1973 Day ............... A61B 5/04012
340/870.21
5,564,428 A    10/1996 Soernmo et al.
(Continued)

OTHER PUBLICATIONS

Afonso et al., "ECG beat detection using filter banks," IEEE Transactions on Biomedical Engineering, 46(2):192-202 (1999).
(Continued)

*Primary Examiner* — Carl H Layno
*Assistant Examiner* — Jon Eric C Morales
(74) *Attorney, Agent, or Firm* — Wenderoth, Lind & Ponack, L.L.P.

(57) ABSTRACT

A patient monitoring apparatus and method is provided. A plurality of moving average filters each receive a signal sensed from a patient and generates an output signal including a respective cutoff frequency. An extraction processor is coupled to receive the sensed signal and output signals from each moving average filters. The extraction processor determines at least one feature associated with the sensed signal based on at least one of the sensed signal and the output signals from each moving average filter and generates a feature signal including data representative of the determined at least one feature. A classification processor identifies a position of artifacts within the sensed signal based on the feature signal and generates a signal identifying the position of the artifacts.

21 Claims, 9 Drawing Sheets

(52) U.S. Cl.
CPC ............ *A61B 5/725* (2013.01); *A61B 5/7207* (2013.01); *A61B 5/7264* (2013.01); *A61B 5/7282* (2013.01)

(58) Field of Classification Search
USPC ........................................................ 600/509
See application file for complete search history.

(56) References Cited

U.S. PATENT DOCUMENTS

| | | | |
|---|---|---|---|
| 6,216,031 B1 | 4/2001 | Findeis et al. | |
| 2008/0275353 A1* | 11/2008 | Bartal | A61B 5/04017 600/509 |
| 2011/0184297 A1* | 7/2011 | Vitali | A61B 5/04017 600/509 |

OTHER PUBLICATIONS

Chiarugi et al., "Adaptive threshold QRS detector with best channel selection based on a noise rating system," Computers in Cardiology, 34:157-160 (2007).

Cifford et al., "Signal quality indices and data fusion for determining clinical acceptability of electrocardiograms," Physiological Measurement, 33:1419-1433 (2012).

Hayn et al., "QRS detection based ECQ quality assessment," Physiological Measurement, 33:1449-1461 (2012).

International Search Report and Written Opinion for Application No. PCT/US2015/029521, dated Jul. 22, 2015.

Janjarasjitt, "A new QRS and ECG signal extraction technique for fetal monitoring," Dissertation Case Western Reserve University, May 2006, pp. 1-170.

Kaiser et al., "Artifact processing during exercise testing," Journal of Electrocardiology, 32:212-219 (1999).

Marchesi et al., "ECG processing algorithms for portable monitoring units," The Internet Journal of Medical Technology. Retrieved online Aug. 8, 2013, <http://archive.ispub.com:80/journal/the-internet-journal-of-medical-technology/volume-1-number-2/ecg-processing-algorithms-for-portable-monitoring-units.html>, 8 pages.

Pan et al., "A real-time QRS detection algorithm," IEEE Transactions on Biomedical Engineering, BME-32(3):230-236 (1985).

Peng et al., "Feature selection based on mutual information: criteria of max-dependency, max-relevance, and min-redundancy," IEEE Transactions on Pattern Analysis and Machine Intelligence, 27(8):1226-1238 (2005).

\* cited by examiner

DETECTING ARTIFACTS IN A SIGNAL

CROSS REFERENCE TO RELATED APPLICATIONS

This application is a national stage application, filed under 35 U.S.C. § 371, of International Application No PCT/US2015/029521, filed May 6, 2015, which claims priority under 35 U.S.C. § 119(e) to U.S. provisional patent application no. 61/990,180, filed May 8, 2014, the entire contents of each of which are hereby expressly incorporated by reference in its entirety.

TECHNICAL FIELD

The present subject matter relates generally to the field of electronic devices and, more particularly, to an improved system for detecting artifacts in a signal used in determining a physiological parameter of a patient.

BACKGROUND

The use of electronic devices to perform any number of tasks has steadily increased over time. This is especially true in the field of providing healthcare to patients. In the medical field, patient monitoring devices and/or systems are selectively coupled to a patient via at least one sensor, which senses information from the patient, which is used in deriving at least one physiological parameter associated with the patient.

Different types of patient monitoring devices are able to monitor the physiological state of the patient via at least one electrode applied to the skin of the patient at various locations on the body. For example, the electrical activity of the heart is routinely monitored in clinical environments using an electrocardiogram (ECG) monitor. The ECG monitor is connected to the patient via a plurality of electrodes (sensors) that monitor the electrical impulses emanating from the patient's heart. Wires from the monitor are selectively connected to the electrodes in order to communicate impulses/voltages detected to the ECG monitoring device to provide a healthcare practitioner with data regarding the patient's heart function.

A drawback associated with ECG monitoring relates to the environment in which the monitoring occurs. There are a number of potential sources of interference that exist in the clinical environment. These sources of interference may produce unacceptable noise levels, false beat detections, false beat classifications, and false alarms. While removing all such artifacts is near impossible, there have been attempts to generate and implement a number of artifact detection algorithms to suspend ECG beat detection (and other ECG parameter processing) in the presence of a variety of different types of noise. However, current ECG artifact detection mechanisms are not sensitive enough and result in false alarms caused by mistaking artifacts (such as those caused by patient movement and electrode connectivity issues) as heartbeats. For example, an artifact in the sensed signal may result in the ECG monitor falsely mistaking a portion of the signal for a heartbeat or falsely detecting/identifying the portion of the signal as a QRS complex. This misidentification may result in a number of false alarms including increased heart rate, high PVC runs, ventricular tachycardia, and others. The incorrect measures lead to false alarms and contribute to the clinical problem of alarm fatigue, wherein clinicians become desensitized to overactive alarms.

One approach for identifying artifacts in sensed signals is to discretely identify individual types of artifacts. For example, previous algorithms identify three types of artifacts—high-frequency, characterized by excessive spikes; low-frequency, characterized by large discontinuities; and baseline, characterized by gradual "wandering" away from the typical DC value. Examples of these can be seen in FIG. 1A-1C, respectively. To accomplish this, prior algorithms employ hard thresholds to time-domain features, each of which is designed to catch one and only one of these different artifact types.

As seen in FIG. 1A, "high-frequency" (HF) artifacts are characterized by large numbers of visible spikes, which can easily be mistaken for QRS complexes. This type of artifact is frequently caused by muscle artifacts from patient movements, and can also be caused by electrostatic discharge or power line interference. In the time domain, the number of spikes detected in a given interval can be used to detect these types of artifacts. The goal of a high frequency artifact detection algorithm is to detect a large number of spikes in a small interval.

In contrast to the numerous small spikes that characterize our "high-frequency" artifacts shown in FIG. 1A, low frequency (LF) artifacts can be identified by large jumps in baseline values as shown in FIG. 1B. These discontinuities do in fact produce energy at both high and low frequencies, but conventional LF artifact detection algorithms specifically identify the large displacement from 0. An exemplary LF artifact detection algorithm searches for any extended interval whose voltage is entirely above a fixed threshold over a predetermined period of time. This type of LF artifact detection algorithm is especially useful in detecting artifacts caused by poor electrode connections. A drawback associated with LF artifact detection relates to instances where large QRS complexes are present such as seen during premature ventricular contractions (PVC). One must be careful that these larger QRS complexes that may exceed the voltage threshold are not erroneously labeled as artifacts.

Baseline (BS) artifacts, as seen in FIG. 1C, are characterized by a slow change, often sinusoidal, in the isoline value of the ECG signal. However, even in the presence of large baseline artifacts, as seen in the given example, individual beats can still be readily identified both visually and by certain beat classification algorithms. Certain filtering techniques identify regions of rapid change (typical of QRS complexes) which greatly reduce the impact of this type of artifact. When a baseline artifact is detected, QRS classification and arrhythmia detection may be suppressed, but beat detection remains intact. The BS artifact detection algorithm is similar to LF artifact detection with the differences relating to the voltage thresholds against which the signal is compared. More specifically, the voltage threshold used in BS artifact detection is much lower than the threshold used in LF artifact detection (e.g. in LF artifact detection, the threshold may be ±2 mV whereas the threshold in BS artifact detection may be ±0.5 mV relative to the isoline). Additionally, an the amount of time the ECG signal must spend outside of the voltage thresholds is much longer than a QRS complex before a baseline artifact can be declared by the BS artifact detection algorithm.

Other artifact detection algorithms employ a weighted sum of two input channels used to detect QRS complexes. In these algorithms, the weights assigned to each channel are dependent on the respective waveform amplitudes and noise levels. These algorithms determine the best lead through a normalized distance metric applied to the area under the QRS complex, referred to as the "mismatch". Once the mismatch values are calculated for each QRS complex, they are stored in a histogram structure. This allows the lead selection process to capture a snapshot of the consistency of the QRS complex over time.

Further artifact detection algorithms depend on a finite impulse response residual filter (FRF), which relies on two finite impulse response (FIR) filters—a highpass filter and a lowpass filter in series—to aggressively filter out the residual of the ECG after subtraction of the median beat. Once the ECG signal has been filtered, a switch is applied to select the two best quality leads for beat identification and arrhythmia analysis. Thus, the determination of quality relies on the amplitudes of the detected QRS complexes, the amount of noise present in the signal after filtering, and the electrode connectivity.

While the above list certain examples of artifact detection algorithms, each still maintain the known drawback of insufficient sensitivity resulting in a number of false alarms caused by mistaking artifacts such as those caused by patient movement and sensor connectivity issues as heartbeats. It is thus highly desirable to identify portions of the signals likely to contain artifacts and suspend patient parameter processing on those portions of the signal. A system according to the current subject matter addresses the deficiencies associated with deriving patient parameters from a signal sensed by a sensor.

SUMMARY

In an aspect, a patient monitoring apparatus is provided. A plurality of moving average filters is provided. Each of said plurality of filters receives a signal sensed from a patient and generates an output signal including a respective cutoff frequency. An extraction processor is coupled to receive the sensed signal and output signals from each of the plurality of moving average filters. The extraction processor determines at least one feature associated with the sensed signal based on at least one of the sensed signal and the output signals received from each of the moving average filters and generates a feature signal including data representative of the determined at least one feature. A classification processor identifies a position of artifacts within the sensed signal based on the feature signal and generates a control signal identifying the position of the artifact.

In another aspect, a method of detecting artifacts in a signal sensed by at least one sensor connected to a patient is provided. The method includes receiving the sensed signal at a plurality of moving average filters and for each of the plurality of moving average filters, filtering the received sensed signal to generate respective output signals including a respective cutoff frequency. An extraction processor receives the sensed signal and respective output signals from each of the plurality of moving average filters and determines at least one feature associated with the sensed signal based on at least one of the sensed signal and the output signals received from each of the moving average filters. A feature signal including data representative of the determined at least one feature is generated and a classification processor identifies a position of artifacts within the sensed signal based on the feature signal. The classification processor generates a control signal identifying the position of the artifact.

One or more of the following features can be included in any feasible combination. For example, a patient parameter processor can be included that suspends a determination of at least one patient parameter from the sensed signal based on the identified position of the artifact. Each of the plurality of moving average filters can generate the output signal for a predetermined number of samples within a window of time having a predetermined length. A summer can be included that combines the sensed signal and an output of one of the plurality of moving average filters to generate a first bandpass signal having a predetermined frequency range. A second of the plurality of the moving average filters can receive the first bandpass signal from the summer to generate a second bandpass signal having a second predetermined frequency range. The at least one feature can include a relative power within a predetermined frequency range, the relative power being determined by dividing the power in the second bandpass signal by the power in the first bandpass signal in real time. The at least one feature can include a relative power in a baseline signal. The relative power in a baseline signal can be determined by: $1-(S1/S2)$, where $S1$ is the power in an output signal of a first of the plurality of moving average filters and $S2$ is the power in the sensed signal. Dividing of the power in the second bandpass signal by the power in the first bandpass signal can occur in real time.

The extraction processor can generate the feature signal based on the sensed signal. The feature signal can include data representative of at least one of (a) a skewness value of the signal within the detection window; (b) a kurtosis value of the signal within the detection window; (c) an amount of energy in the U3 operator of the signal; and (d) the detection of a flatline in the detection window. The extraction processor can generate the feature signal based on the output signals of the moving average filters. The feature signal can include data representative of at least one of (a) relative power in a first predetermined frequency band and (b) a relative power in a baseline of the sensed signal. A differentiation processor can be coupled to the extraction processor. The differentiation processor can receive the sensed signal and can generate a differentiation signal based on data representative of a first difference between successive samples of the sensed signal and data representative of a second difference between successive samples of the first difference. The extraction processor can generate the feature signal based on at least one of the sensed signal, the output signals of the moving average filters, and the differentiation signal. The classification processor can be a dynamic neural network that determines a classifier value from the feature signal and identifies the position of the artifacts when the determined classifier value one of exceeds or falls below a threshold value. The classification processor can identify the temporal position of the one or more artifacts within the sensed signal in real time.

A patient parameter processor can suspend a determination of at least one patient parameter from the sensed signal based on the identified position of the artifact. For each of the plurality of moving average filters, the output signal can be generated for a predetermined number of samples within a window of time having a predetermined length. The sensed signal and an output of one of the plurality of moving average filters can be combined using a summer to generate a first bandpass signal having a predetermined frequency range. The first bandpass signal from the summer can be received at a second of the plurality of the moving average filters. A second bandpass signal having a second predetermined frequency range can be generated. Determining at least one feature can include determining a relative power within a predetermined frequency range by dividing the power in the second bandpass signal by the power in the first bandpass signal in real time. Determining the at least one feature can include determining a relative power in a baseline signal by: 1−(S1/S2), where S1 is the power in an output signal of a first of the plurality of moving average filters and S2 is the power in the sensed signal. Dividing of the power in the second bandpass signal by the power in the first bandpass signal occurs in real time.

The feature signal can be generated by the extraction processor and based on the sensed signal. The feature signal can include data representative of at least one of (a) a skewness value of the signal within the detection window; (b) a kurtosis value of the signal within the detection window; (c) an amount of energy in the U3 operator of the signal; and (d) the detection of a flatline in the detection window. The extraction processor can generate the feature signal based on the output signals of the moving average filters. The feature signal can include data representative of at least one of (a) relative power in a first predetermined frequency band and (b) a relative power in a baseline of the sensed signal.

The sensed signal can be received at a differentiation processor coupled to the extraction processor. A differentiation signal can be generated based on data representative of a first difference between successive samples of the sensed signal and data representative of a second difference between successive samples of the first difference. The feature signal can be generated by the extraction processor and based on at least one of the sensed signal, the output signals of the moving average filters, and the differentiation signal. Identifying can include determining a classifier value from the feature signal using a dynamic neural network; and identifying the position of the artifacts when the determined classifier value one of exceeds or falls below a threshold value. Identifying the temporal position of the one or more artifacts within the sensed signal can be in real time.

DETAILED DESCRIPTION

Figure 1A:
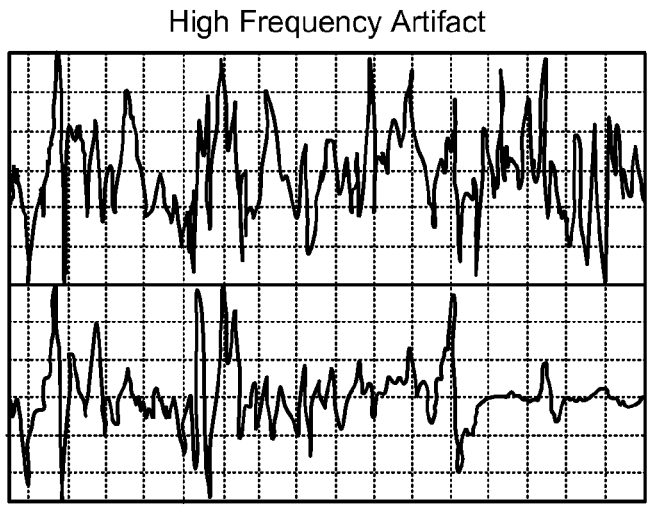
FIGS. 1A-1C are waveform illustrations of types of artifacts that may be present in a signal.
Figure 1B:
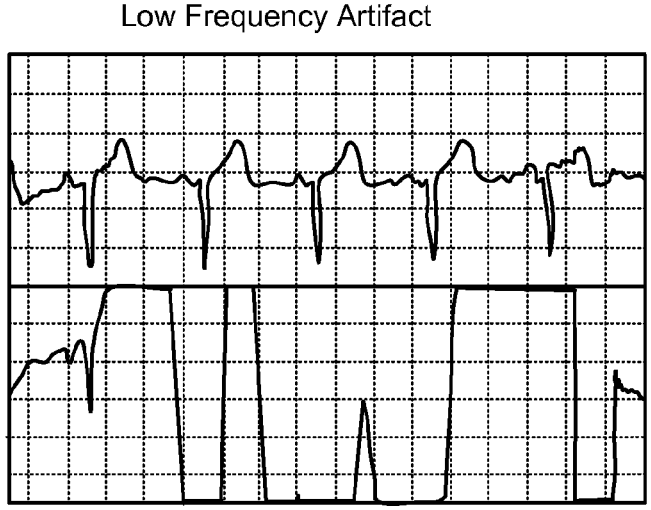
Figure 1C:
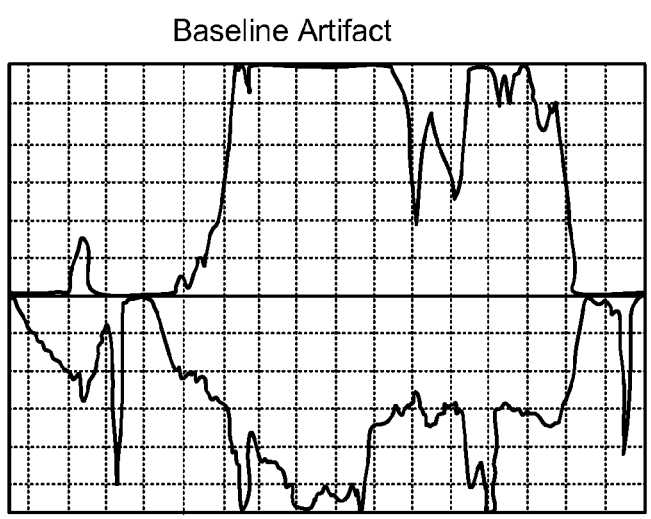

An apparatus and method for identifying artifacts in a signal sensed by a patient connected sensor can be provided. Exemplary types of artifacts that may be identified include, but are not limited to, at least one of (a) high frequency artifacts; (b) low frequency artifacts; and (c) baseline artifacts. The apparatus, according to the current subject matter, advantageously derives at least one feature from the sensed signal and uses the derived at least one feature to identify the presence of artifacts within the given signal over a detection window having a predetermined length. The apparatus may advantageously simultaneously identify a plurality of types of artifacts present in the signal. In response to identifying the artifacts in the signal, certain other processing features of the apparatus may be suppressed in order to conserve system resources by minimizing processing on signals deemed to be of insufficient quality due to the presence of artifacts therein.

To identify and detect the presence of artifacts in the signal sensed by the patient connected sensors, a set of filters for filtering signals in the time domain are provided. Each filter of the set of filters includes a different cutoff frequency and operates in accordance with a first type of filtering technique is employed to filter portions of the signal at the respective cutoff frequencies. In one embodiment, the first type of filtering technique is a moving average filtering technique. The outputs of each filter of the set of filters are input to a feature extraction processor. The feature extraction processor uses the filtered signals to calculate at least one type of feature associated with the signal. In one embodiment, at least one type of feature includes at least one of (a) a relative power in a first frequency band of the signal; and (b) a relative power after cutoff at a predetermined frequency. The feature extraction processor outputs data representing each type of feature extracted from the filtered signals as feature output data thereby defining a feature space for the signal being processed. The feature output data is provided to a classification processor that classifies the features, in real-time, to determine a level of importance for respective features in identifying artifacts in a signal. The classification processor assigns weighted values to each of the respective feature output data received thereby and employs a pattern classification technique to reduce the feature space from a multidimensional feature space into a two dimensional feature space. The feature classifier may then be compared to a single threshold that is indicative of the presence of an artifact which may be used to suppress further processing of the sensed signal by any other component of the apparatus. In one embodiment, if the feature classifier meets or exceeds the threshold, the feature classification processor suppresses further processing by a parameter processor used to derive patient parameter data from the sensed signal. For example, the parameter processor may be configured to execute at least one of a beat classification algorithm and a QRS complex detection algorithm and, upon determining the feature classifier exceeds the threshold, the classification processor may suppress the execution of any algorithms executed by the parameter processor. This suppression advantageously minimizes false alarms regarding patient conditions. This suppression also advantageously improves processing and operating efficiency of the apparatus by suppressing processing of an input signal determined to be of insufficient quality.

In another embodiment, the feature extraction processor also extracts certain features from the unfiltered signal. The features extracted from the unfiltered signal are provided, in conjunction with the features extracted from the filtered signal, to the classification processor. By providing features from the unfiltered signal along with features from the filtered signal, a greater feature space is created thereby advantageously improving the ability of the artifact classification algorithm to identify artifacts present in the unfiltered signal. The classification processor assigns a weighted value to each respective feature output data received thereby and employs a pattern classification technique to reduce the feature space from a multidimensional feature space into a two dimensional feature space as discussed above.

Figure 2:
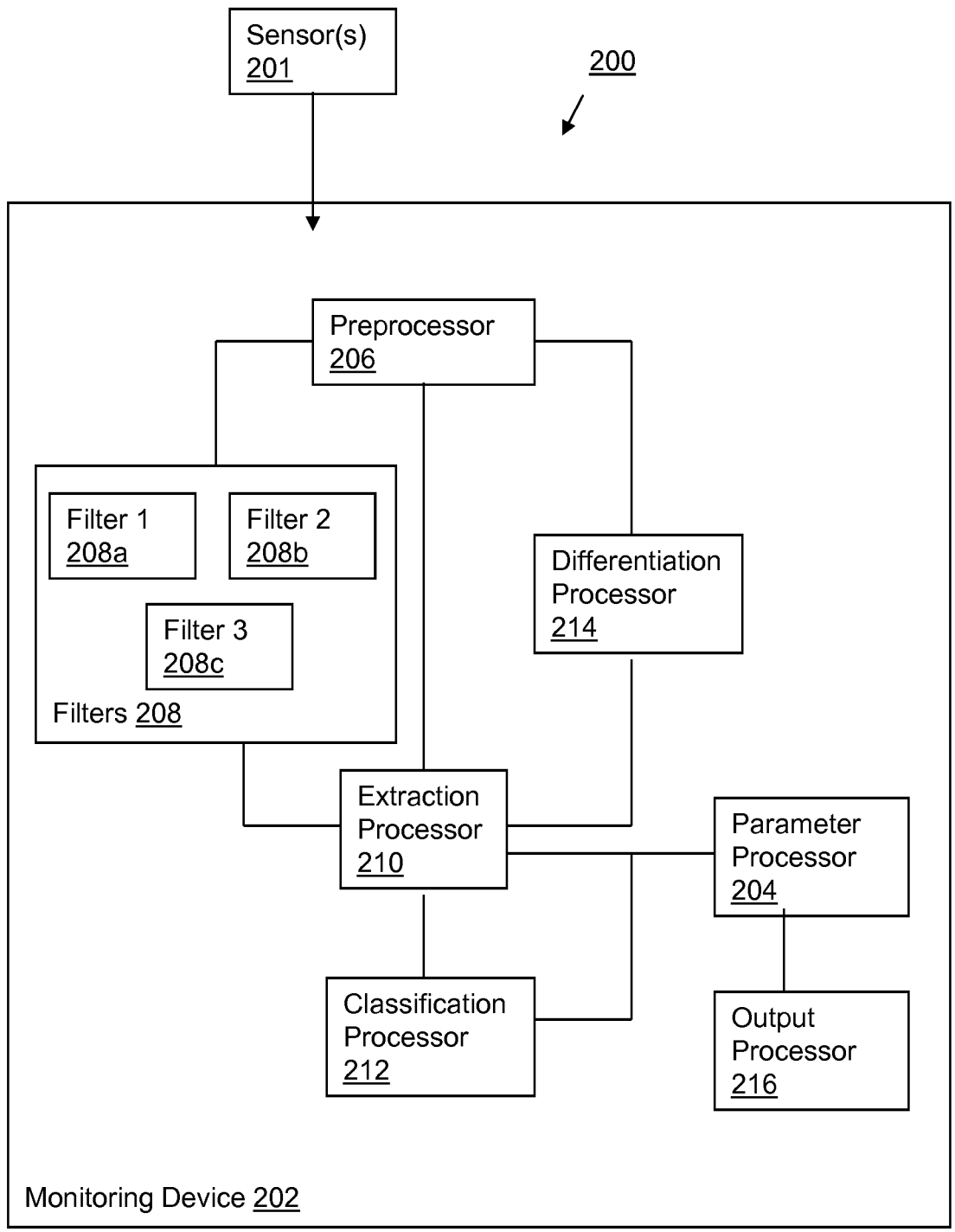
FIG. 2 is a block diagram of device for identifying artifacts in a signal according to the current subject matter.

An exemplary apparatus 100 for identifying artifacts in a signal is provided in FIG. 2. The apparatus 200 of FIG. 2 may be a patient monitoring device 202 having at least one type of patient connected sensor 201 connected thereto for sensing a signal from the patient. In one embodiment, the patient monitoring device is an electrocardiogram monitoring (ECG) device and the sensors 201 are a set of electrodes connected to the patient in any known configuration. In other embodiments, the sensors 201 may be any type of physiological sensor able to sense a signal from a patient for use in generating ECG data for the patient. In another embodiment, the patient monitoring device is programmed to monitor multiple patient parameters simultaneously. In this embodiment, the device may multiple patient connected sensors for sensing different types of signals from the patient that may be used to determine a plurality of different patient parameters. In this embodiment, one of the patient parameters monitored by the patient monitoring device includes ECG data and the at least one other patient parameter may include blood oxygenation (SpO2) data. These are provided for purposes of example only and the patient monitoring device 202 may be specifically programmed to determine and monitor any type of patient parameter using any type of patient connected sensors conventionally associated with monitoring the respective type of patient parameter.

The patient monitoring device 202 includes a parameter processor 204 for selectively processing the signals sensed by the at least one sensor 201 to determine a plurality of different patient parameters. The parameter processor 204 represents circuitry that is specifically programmed to store executable instructions that implement at least one type of patient parameter processing algorithm that uses data contained in the sensed signal to derive respective types of patient parameter data that may be output to a clinician via an output processor 216. The output processor 216 may receive and format for display the patient parameter data determined by the parameter processor 204. In another embodiment, the output processor 216 may comprise communication functionality and generate a message including the patient parameter data. The output processor 216 selectively connects to a communication network to communicate the message to a remote system (e.g. a healthcare information system, a central monitoring station, etc). Once communicated, the patient parameter data in the message may be used by a clinician to support the delivery of healthcare to the patient.

To derive the patient parameter data used in supporting the delivery of healthcare to a patient, the patient monitoring device 202 includes a plurality of components that process and/or modify the signals sensed by the sensors 201. The patient monitoring device 202 includes a preprocessor 206 which receives the signal sensed by sensors 201. The signal sensed by the sensors 201 are sampled at a first predetermined sampling rate and the preprocessor 206 receives the signal and downsamples the signal from the first predetermined sampling rate to a second lower predetermined sampling rate. The patient monitoring device 202 samples the input signal at the first predetermined sampling rate in order to identify the presence of a first kind of signal that cannot be further processed by the patient monitoring device to determine the patient parameter. More specifically, the patient parameter processing algorithms require the input signal be sampled at the second predetermined sampling rate in order to properly determine the respective patient parameter data therefrom in view of the computational expense required to compute these patient parameters at the first higher predetermined sampling rate. Additionally, the preprocessor 206 employs at least one of a low pass filter and notch filter to produce a preprocessed signal. In an embodiment where the patient monitoring device 202 is an ECG monitor (or multiparameter monitor including ECG monitoring capabilities), the signal sensed by the sensors 201 is sampled at 16 kHz which is necessary to detect the presence of sharp spikes commonly produced by a pacemaker. In this embodiment, the preprocessor 206 further filters the input signal sensed by the sensors 201 using a notch filter to remove common mode and power line noise and uses a low pass filter to generate the preprocessed signal having a frequency range between 0 and 40 Hz.

The preprocessed signal is output at a first output terminal of the preprocessor 206 and provided to a set of filters 208. The set of filters 208 include at least one filter for further filtering the preprocessed signal to yield a filtered signal having a characteristic determined by the parameter of the at least one filter in the set of filters 208. The set of filters 208 includes a set of moving average filters for filtering the preprocessed signal in the time domain thereby maximizing computational efficiency enabling real-time monitoring of signals sensed by the sensors 201 for the presence of artifacts. A moving average filter takes the average over an n sample window for every sample in the preprocessed signal to generate a vector representing a collection of the averages which approximates a LPF (low-pass filter) version of the signal with cutoff of approximately $F_s/n$ Hz, where $F_s$ is the sampling frequency in Hertz. Additionally, the moving average filter may be used to compute a highpass version of the same signal by subtracting the moving average signal from the original signal. Furthermore, by using the output of one or more moving average filters, bandpass filters can be approximated by using highpass and lowpass filters with different cutoff frequencies.

In the embodiment shown in FIG. 2, the set of filters 208 includes a first filter 208a, a second filter 208b and a third filter 208c. The filter parameter associated with each of the filters 208a-208c represents a different cutoff frequency. The first filter 208a includes a first cutoff frequency able to provide a low pass filtered version of the preprocessed signal as a first filtered output signal. The second filter 208b includes a second cutoff frequency that is greater than the first cutoff frequency and provides a second filtered output signal. The third filter 208c includes a third cutoff frequency that is greater than both the first cutoff frequency and the second cutoff frequency and produces a third filtered output signal. Each of the first, second and third filtered output signals may be provided to an extraction processor 210 which calculates at least one feature associated with the preprocessed signal based on the at least one of the first filtered output signal, the second filtered output signal and the third filtered output signal. In another embodiment, the filters 208 may include a summer that can combine any of the first, second and/or third filtered output signals to generate at least one bandpass filtered output signal by subtracting any of the filtered output signals from at least one of (a) the preprocessed signal (which is a substantially full spectrum signal); and (b) any of the other filtered output signals. In one example, a first bandpass filtered output signal may be generated by subtracting the second filtered output signal from the preprocessed signal. The first bandpass filtered output signal will have a frequency range with a lower bound being defined by the second cutoff frequency and an upper bound being defined by the upper bound of the preprocessed signal. In another example, a second bandpass filtered output signal may be generated by subtracting the second filtered output from the preprocessed signal and providing the difference as an input to the third filter 208c. The resulting second bandpass filtered output signal filtered by the third filter 208c has a frequency range with a lower bound being defined by the second cutoff frequency and an upper bound being defined by the third cutoff frequency of the third filter 208c. Any of the first, second and/or third filtered output signals and/or the first and second bandpass output signals are provided to an extraction processor 210 (discussed in greater detail below) that uses these signals to compute features associated with the signal sensed by the sensors 201. The above description of three filters and the output signal and bandpass signals generated thereby are provided for purposes of example only and the set of filters 208 may include any number of moving average filters having different filter parameters thereby enabling output of various filtered output signals which may be used to calculate any number of features associated with the signal sensed by the sensors 201.

The extraction processor 210 selectively receives at least one of (a) the first filtered output signal; (b) the second filtered output signal; (c) the third filtered output signal; (d) the first bandpass filtered output signal; and (e) the second bandpass filtered output signal, collectively referred to as the filtered signals. From at least one of the filtered signals, the extraction processor uses a feature extraction algorithm in order to determine at least one feature associated with the signal being sensed by the sensors 201. The extraction processor 210 determines features by defining a detection window having a first duration and computing the moving average over the first n points of the detection window. The moving average moves one point at a time through the entire detection window and when all features have been computed over the original detection window, the window shifts by k/2 seconds, where k is the duration of the detection window and the process is repeated. This enables partial overlap of portions of the signal between successive detection windows thereby providing a more accurate determination of the feature at a given point in the detection window. Thus, depending on the feature being calculated by the extraction processor 210, any of the filtered signals are used in the detection window to calculate the respective feature.

The features determined by the extraction processor 210 are output as a feature signal. The feature signal is generated by the extraction processor 210 using the filtered signals discussed above which are output by the various moving average filters and includes at least one of (a) an amount of energy contained within a particular frequency band of the preprocessed signal; (b) a relative power value of a predetermined frequency band; and (c) a relative power value of a baseline signal. In one exemplary embodiment, the relative power of a predetermined frequency band is determined by dividing the power in the second bandpass filtered output signal by the power in the first bandpass filtered output signal. In another exemplary embodiment, the relative power value of the baseline signal is determined by dividing the power in the first filtered output signal by the power in the full spectrum preprocessed signal. The extraction processor 210 may also determine additional relative power features of the signal. In one example, a relative power feature may be determined by first subtracting the third filtered output signal from the preprocessed signal to obtain a third bandpass filtered output signal and dividing the power in the second filtered output signal by the power in the third bandpass filtered output signal. In another example, a relative power feature may be determined by dividing the power in the second filtered output signal by the power in the first bandpass filtered output signal. In a further example, a relative power feature may be determined by dividing the power in the first bandpass filtered output signal by the power in the preprocessed signal. A relative power feature may also be determined by including a fourth moving average filter that has a fourth frequency cutoff between the frequency cutoff of the second filter 208b and a frequency cutoff of the third filter 208c to produce a fourth filtered output signal. In this example, the fourth filtered output signal may be subtracted from the preprocessed signal to produce a fourth bandpass filtered output signal which may be divided by the full spectrum preprocessed signal to yield the relative power feature of interest.

The patient monitoring device 202 also includes a classification processor 212 coupled to the extraction processor 210. In response to determining a plurality of features associated with the signal sensed by the sensors 201, the classification processor 212 generates a control signal. The control signal generated by the classification processor 212 advantageously determines a classifier that identifies, for respective temporal positions in the sensed signals, whether a particular section of the signal sensed by the sensors includes artifacts. The indication that artifacts are present means that the particular section contains noise and should not be used in determining the patient parameter being monitored by the patient monitoring device 202. The classification processor 212 employs a pattern classification algorithm which is stored therein. The pattern classification algorithm executed by the classification processor 212 should be able to draw a series of hyperplanes to divide the feature space into regions of arbitrary shape. In an exemplary embodiment, the classification processor 212 performs pattern classification to determine the classifier using a dynamic neural network. In the present circumstances where the objective is to identify artifacts over a period of time within a particular detection window, a dynamic neural network provides an advantage over static neural networks because of the time-varying nature of the artifacts being detected. Whereas static classification systems can only learn time-independent weights to apply to the extracted features, a dynamic classifier can learn and apply time-dependent weights. This allows dynamic classifiers to be trained to learn how the features change in the presence of artifacts over time. In contrast, static classifiers are constrained to learning from single snapshots of the features at a particular moment. The use of a dynamic neural network is described as one exemplary algorithm for determining a classifier. Other pattern classification algorithms that may be stored and executed by the classification processor 212 include any of (a) support vector machine; and (b) hidden Markov model classification techniques.

It is important to note the parameters of the dynamic neural network used to classify the features data obtained from the extraction processor 210 has been trained and validated using a set of data representative of the signal types that are being sensed by the sensors. During the training process, the dynamic neural network learns the relationship between the inputs comprising the features to be determined by the extraction processor 210 and the desired output representing a classifier that indicates whether the features over a particular detection window are indicative of an artifact (or other noise) in the signal. The learning that occurs during the training process may be characterized as the updating of connection weights in order to gradually reduce the difference between the desired network output and the current output. Specifically, the weights are adjusted through the use of training data patterns presented to the neural network, which result in performance improvements through iterative updating of the weights. The particular mechanisms for training a dynamic neural network are known in the art and need not further be discussed. The key point is that the set of training data represents the type of signal being sensed and monitored by the particular patient monitoring device includes the features that will be extracted in real-time by the extraction processor 210 when active monitoring of the sensed signal occurs.

In operation, and upon completion of the training process, the classification processor 212 generates the control signal by executing instructions representing scalar weights and biases to be applied to each feature extracted by the extraction processor 210. The classification processor 212 assigns the stored weights and biases to vectors representing a set of values of each type of feature extracted by the extraction processor 210 and multiplies the weighted vectors to yield a classifier. The classifier is compared to a threshold value and if it exceeds the threshold value, the classification processor 212 identifies that temporal position in the sensed signal and flags the portion of the signal as including an artifact. The classified data including the signal data and any flags indicative of artifacts is provided to the parameter processor 204 which uses the flags to cease processing the flagged portion of the signal for patient parameter data thereby conserving computational and other system resources.

In one embodiment, a differentiation processor 214 is also connected to the preprocessor 206. The differentiation processor 214 includes a difference buffer for storing data representing successive samples of the preprocessed signal output by the preprocessor. The samples are stored in the buffer of the differentiation processor 214. The differentiation processor 214 determines data representing a first difference and data representing a second difference. The data representing the first difference and second difference are output as a differentiation signal by the differentiation processor 214. Data representing the first difference is calculated by obtaining a difference between the first two samples stored in the buffer. Thereafter, the second difference is calculated by the differentiation processor 214 by obtaining a difference between a next sample in the buffer and the first difference value calculated above. These calculations are repeated for all samples stored in the buffer at a given time. The data representing the first difference and second difference are provided to the extraction processor 210 which uses this data to calculate at least one feature therefrom. Exemplary features able to be calculated by the extraction processor 210 include at least one of (a) total energy in the first difference value; (b) total energy in the second difference value; (c) total energy in the difference buffer; (d) standard deviation of samples in the difference buffer; (e) total energy in the absolute second difference value; (f) a maximum value in the difference buffer; and (f) a sum of the values in the difference buffer. Any of the features determined by the extraction processor 210 based on data stored in the difference buffer and/or the first and second difference values may be used as inputs to the pattern classification algorithm executed by the classification processor 212 in the manner discussed above.

In another embodiment, the preprocessor 206 outputs the preprocessed signal directly to the extraction processor 210. The extraction processor 210 also determines at least one feature directly from the samples in the preprocessed signal which may be used as additional inputs to the classification algorithm executed by the classification processor 212. The at least one feature determined directly from the preprocessed signal includes at least one of (a) maximum value in the raw signal buffer; (b) a sum of values in the raw signal buffer; (c) a result of signal quality index calculation in a U3 operator (d) a maximum value in a U3 operator; (e) a sum of values in a U3 operator; (f) a result of signal quality index calculation in a U3 operator; (g) a difference between maximum and minimum values in a raw signal buffer; (h) a number of peaks in a predetermined window of time; (i) a number of samples >0.5 mV above the baseline value; (j) a number of samples <0.5 mV below the baseline value; (k) a flatline detection indicating that a predetermined percentage (e.g. 40%) of samples have an amplitude greater than a threshold amplitude value; (l) a flatline detection indicating that a predetermined percentage (e.g. 80%) of samples have an amplitude value greater than a threshold amplitude value based on the result of the first difference estimator; (m) a skewness value (e.g. measure of symmetry or lack thereof in a set of data); (n) kurtosis value (e.g. a measure indicating whether data are peaked or flat relative to a normal distribution); and (o) a total energy value of the U3 operator.

A U3 operator is a filter, similar to a differentiator, having high values in the presence of QRS complexes, and lower values in other places. The formula for the n-th sample of a signal y after a U3 operator has been applied is $U3[n] = U3[n-1] - (y[n-w-2] - y[n-w])^2 + (y[n+w-2] - y[n+w])^2$, where w is an adjustable window-length parameter. A value of 12 may be used for w, however, other values may be used.

As discussed above, there are a plurality of different feature types that the extraction processor 210 may extract from any of the preprocessed signals, the filtered output signals, the bandpass signals; and the difference values computed by the differentiation processor 214. It should be understood that the extraction processor 210 may determine all of the features discussed above or only a subset of the features based on an offline determination identifying which of the above described features are most important in identifying the presence of artifacts within a particular detection window. One manner of offline determination used to identify which of the features discussed above provides the strongest likelihood of artifact identification in the signal is by using a set of testing data representative of the signal being sensed by the sensors and determining data representing each of the features listed above generating a feature space having up to 37 dimensions. To reduce the feature space, a linear discriminant analysis (LDA) may be performed which determines the relative importance of the feature in detecting the presence of an artifact. The LDA determines a linear combination of the input features that best discriminate between the different classes of signals.

Thus, the result of LDA will be a vector of weights $\vec{w}$ that, when multiplied with the 37 potential features, produces a single feature that best discriminates between intervals in which an artifact is present and those in which an artifact is absent. While, LDA is typically used to reduce the dimensionality of a high-dimensional feature space before classification, as used herein in determining which features the extraction processor 210 will ultimately extract from the signal, it is used as a measure of the relative importance of the 37 features considered by the classification processor 212. The weight vector $\vec{w}$ produced by LDA assigns a scalar value to each of the 37 features such that the greater the amplitude of the scalar value, the better that feature discriminates between the two classes (e.g. artifact or no artifact). We computed the LDA over the same set of training data (after normalizing the values produced by each feature to the range [−1, 1]) that was used to train the classification algorithm executed by the classification processor 212.

One exemplary embodiment of a type of patient monitoring device 202 described above with respect to FIG. 2 will now be described in greater detail. FIGS. 3-9 describe the current subject matter used in sensing electrophysiological signals from patient connected sensors that are used in determining at least one type of patient parameter associated with the patient's heart. More specifically, the monitoring device according to the current subject matter is an ECG monitoring device or a patient monitoring device able to monitor a plurality of patient parameters where one such parameter is ECG data. The ability and effectiveness of the above discussed algorithm for determining features associated with a signal and, more specifically, energy-related features within the signal, to classify whether a particular portion of the sensed signal includes an artifact can be shown in FIGS. 3A, 3B, 4A and 4B which represent clean and noisy ECG signals in both the time and frequency domain. When considering the signal quality of an ECG signal, the most important portion thereof is the frequency band that includes the QRS complex. The detection and classification of the QRS complex is a key metric used in ECG monitoring devices for determining a host of patient parameter data including, but not limited to, beat detection/classification, ventricular fibrillation (VFIB), atrial fibrillation (AFIB), arrhythmia detection, ST analysis and heart rate. Thus, it is important to ensure that the data being detected as a QRS complex is an actual QRS complex and not an artifact that may have certain characteristic similar to a QRS complex but is not an actual QRS complex.

Figure 3A:
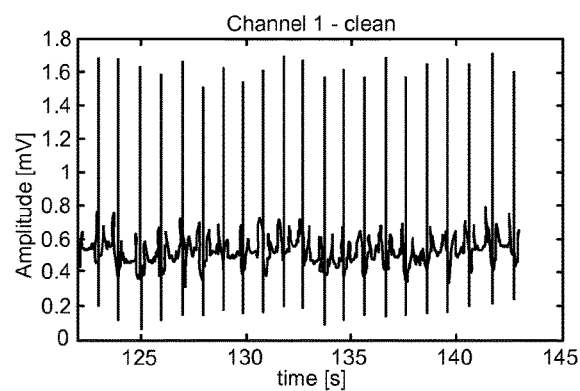
FIG. 3A is an exemplary clean ECG waveform filtered in the time domain.
Figure 3B:
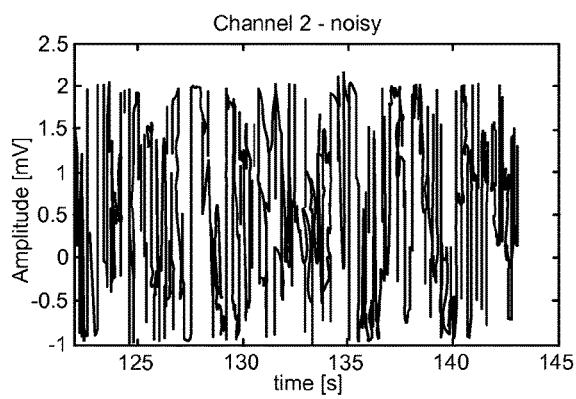
FIG. 3B is an exemplary noisy ECG waveform filtered in the time domain.
Figure 4A:
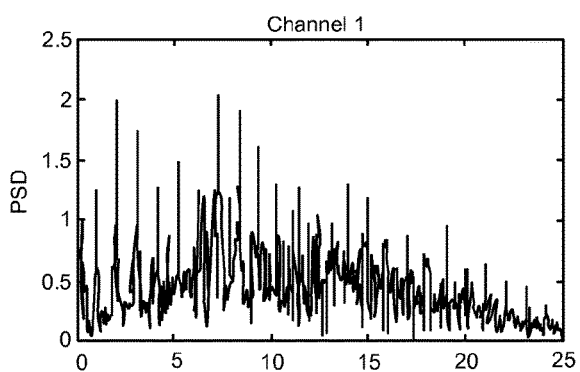
FIG. 4A is an exemplary clean ECG waveform filtered in the frequency domain.
Figure 4B:
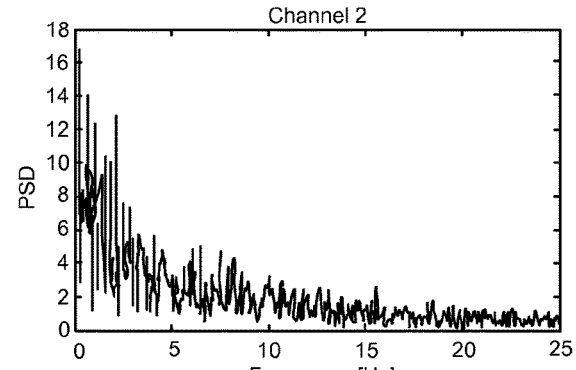
FIG. 4B is an exemplary noisy ECG waveform filtered in the time domain.

In furtherance of the artifact detection and identification, it is important to note that the frequency content between normal QRS complexes (FIGS. 3A and 4A) and noisy regions (FIGS. 3B and 4B) differs substantially. In FIGS. 3A and 4A, the clean ECG signal resembles an impulse train (in both time and frequency representations). However, in FIGS. 3B and 4B, a noisy, artifact-filled region that typically lack this predictable pattern of spikes shown in FIGS. 3A and 4A is shown. Moreover, with respect to the noisy signal in the frequency domain shown in FIG. 4B, there is significantly more power in the lower frequencies as compared to the more even distribution of power in the clean ECG signal in FIG. 4A.

Because of this power distribution, the ECG monitoring device can distinguish these classes (e.g. clean and noisy/artifact) via a power measurement in the "QRS band" which is commonly understood to exist between 5-15 Hz. Additionally, this relationship holds even though the exact frequency distribution can vary for different rhythms (especially between ventricular fibrillation, atrial fibrillation and normal sinus rhythm). In an "offline" (i.e., non-real-time) situation, we could compute the discrete Fourier transform (via an algorithm such as the fast Fourier transform (FFT)) to easily find the total power in this band. However, in a real-time monitoring situation of patient ECG data, the off-line method would be too computationally complex. Thus, the ECG monitoring device according to the current subject matter employs a time domain filtering technique which is sufficient because, according to Parseval's Theorem, the energy in the time domain is substantially equivalent to the energy in the frequency domain. Thus, energy in the frequency band of interest can be approximated by the energy in an appropriately filtered version of the time-domain signal.

Figure 5:
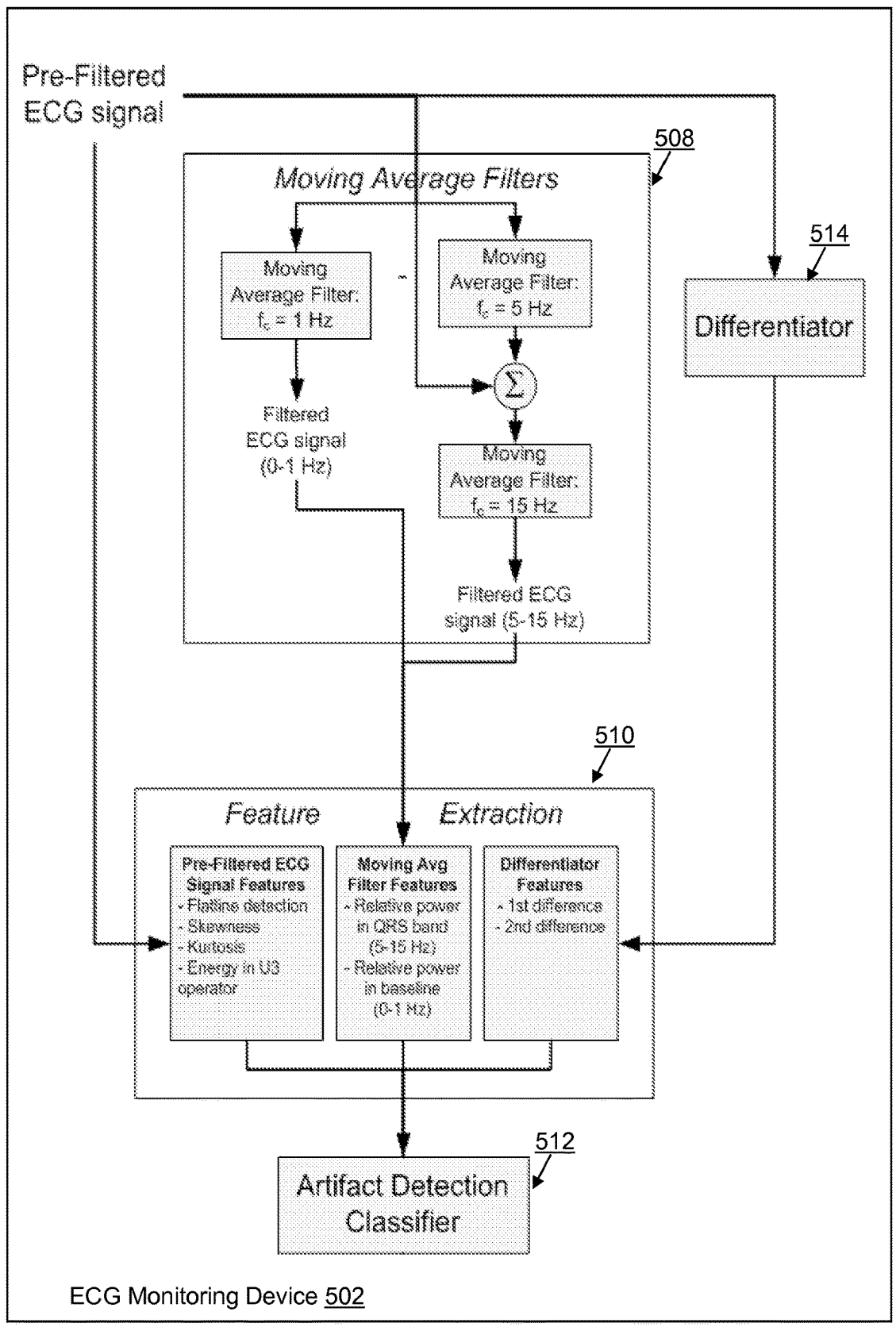
FIG. 5 is a block diagram of an ECG monitoring device that identifies artifacts in an ECG signal according to the current subject matter.

Referring now to FIG. 5, an exemplary ECG monitoring device 502 including the artifact detection system according to the current subject matter is depicted. The block diagram of FIG. 5 includes similar elements as those described above with respect to FIG. 2 and similar components are labeled with similar reference numerals and thus the general operation and description of the similarly numbered components in FIG. 2 are applicable herein and will not be further discussed. However, the description of the components of the ECG monitoring device 502 is intended to supplement the descriptions contained in FIG. 2 in order to tailor the operation to detecting artifacts in an ECG signal.

The block diagram in FIG. 5 omits the sensors 201, preprocessor 206, parameter processor 204 and output processor 216. However, it should be understood that each of those components are also included in the ECG monitoring device 502 and operate in a manner similarly as described above with respect to FIG. 2. Thus, ECG monitoring device 502 receives the input signal sensed by the sensors and preprocessed to be a 40 Hz signal. The ECG signal is collected from electrodes placed on the patient's skin and initially sampled at 16 kHz. This high sampling rate is necessary to detect the sharp spikes commonly produced by pacemakers, for instance. However, to perform the algorithms required for beat classification and arrhythmia detection on this signal would be too computationally expensive. The signal is therefore downsampled to 250 Hz, with anti-aliasing and other lowpass filters applied such that the "pre-filtered ECG signal" referenced has an effective frequency range of 0 to 40 Hz. The preprocessed signal (identified in FIG. 5 as the "pre-filtered signal") is provided simultaneously to the set of moving average filters 508, the differentiator 514 (e.g. differentiation processor in FIG. 2) and the feature extraction module 510. Each of these components process the preprocessed signal in a particular manner in order to determine a set of features associated with the preprocessed signal and used in classifying whether the signal includes any artifacts.

Figure 6:
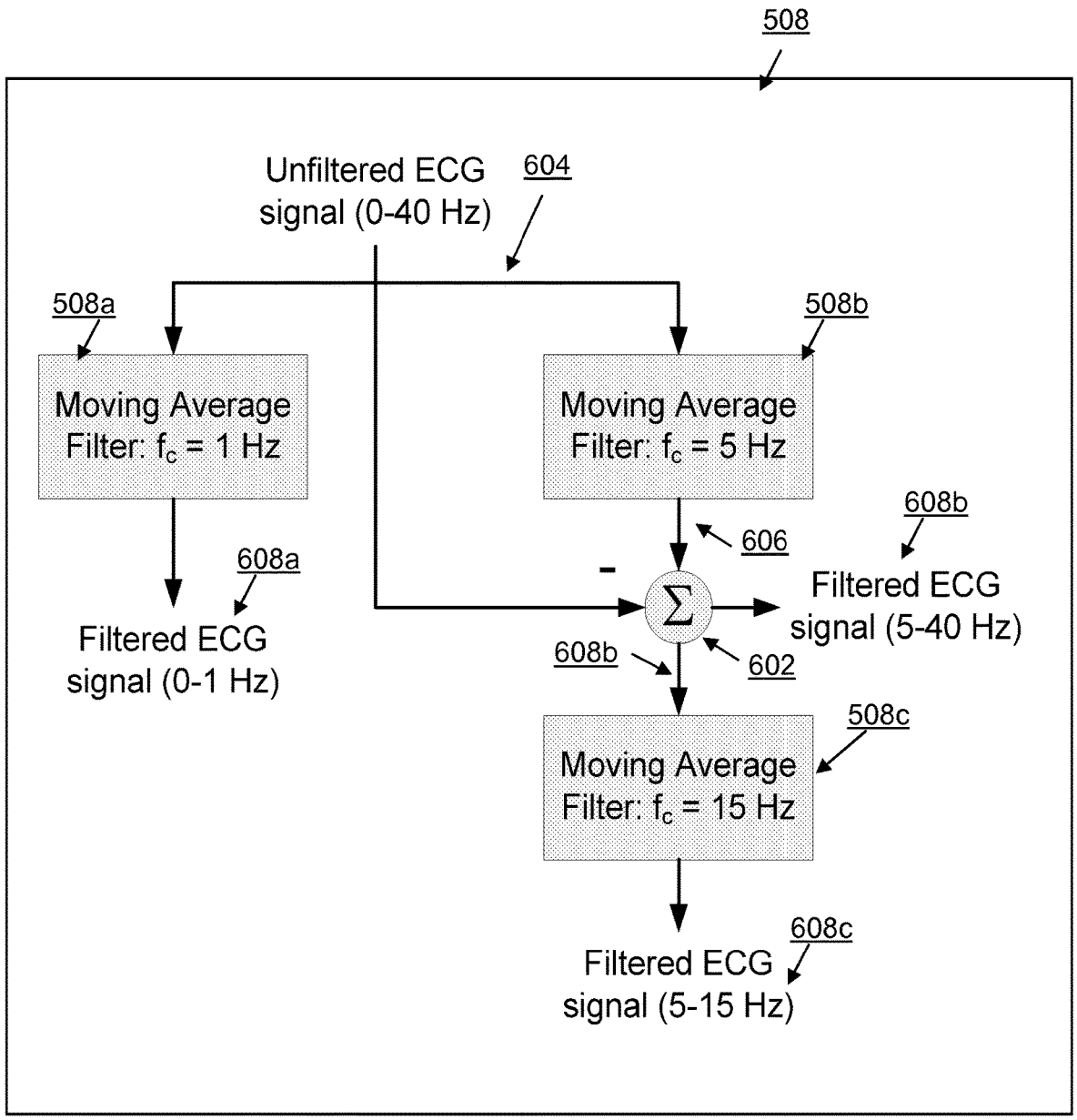
FIG. 6 is a block diagram of a set of filters in the ECG monitoring device of FIG. 5 according to the current subject matter.
Figure 7:
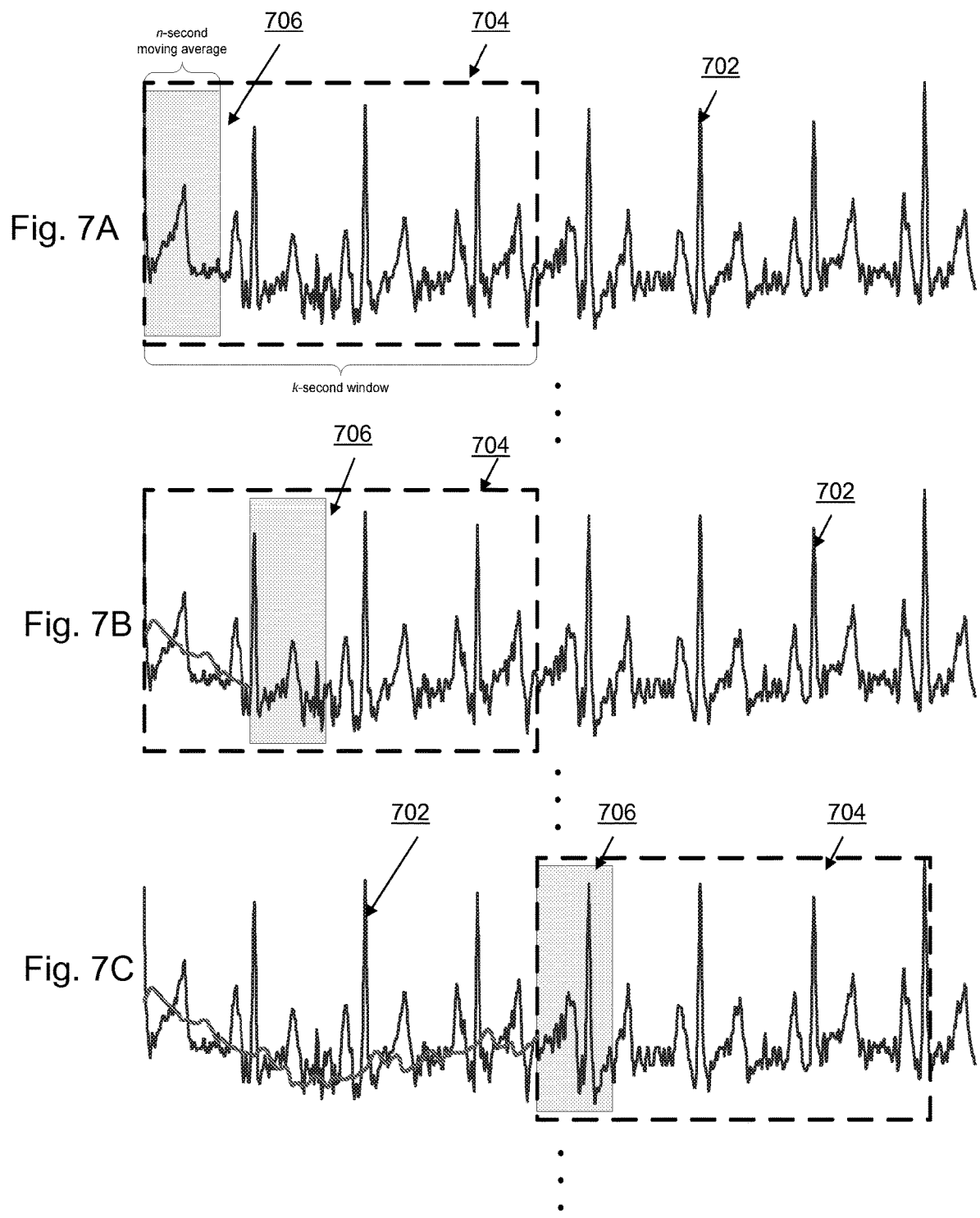
FIGS. 7A-7C are exemplary ECG waveforms processed according to the artifact detection algorithm according to the current subject matter.

The moving average filters 508 operate in a similar manner to the set of filters 208 described above in FIG. 2. The set of moving average filters 508 is shown in greater detail in FIG. 6. As shown in FIG. 6, the set of moving average filters 508 include a first moving average filter 508a having a cutoff frequency ($f_c$) of 1 Hz which, from an input of the preprocessed signal 604 (i.e., the unfiltered ECG signal), produces the first filtered output signal 608a having a frequency range between 0 and 1 Hz. A second moving average filter 508b having a second cutoff frequency of 5 Hz provides, from an input of the preprocessed signal 604, a second filtered output signal 606 having a frequency range between 0 and 5 Hz. The second filtered output signal 606 and preprocessed signal 604 are provided as inputs to a summer 602. By receiving different signals having different cutoff frequencies, the summer 602 enables bandpass filtering of the signals such that the resulting signal output will have upper and lower bounds determined by the frequency cutoff values of the first and second moving average filters.

The summer 602 performs a negative sum of (i.e., a difference between) the second filtered output signal 606 having a frequency range between 0 and 5 Hz and the preprocessed signal 604 having a frequency range between 0 and 40 Hz to generate a first bandpass signal 608b having a frequency ranging between 5 Hz and 40 Hz. The first bandpass signal 608b is then provided to a third moving average filter 508c having a third cutoff frequency of 15 Hz. Thus, the third moving average filter 508c generates a second bandpass signal 608c having a frequency ranging between 5 Hz and 15 Hz. In this embodiment, the first filtered signal 608a, the first bandpass signal 608b and second bandpass signal 608c are provided to the feature extraction module 510 shown in FIG. 5 as input signals used to determine respective features associated with the preprocessed signal 604 as will be discussed below.

The three moving average filters 508a-508c are shown for purposes of example only and any number of moving average filters having different cutoff frequencies may be included, either in parallel or in series, to generate different filtered output signals and/or bandpass signals that may be used as inputs for calculating respective features associated with the signal.

Figure 8:
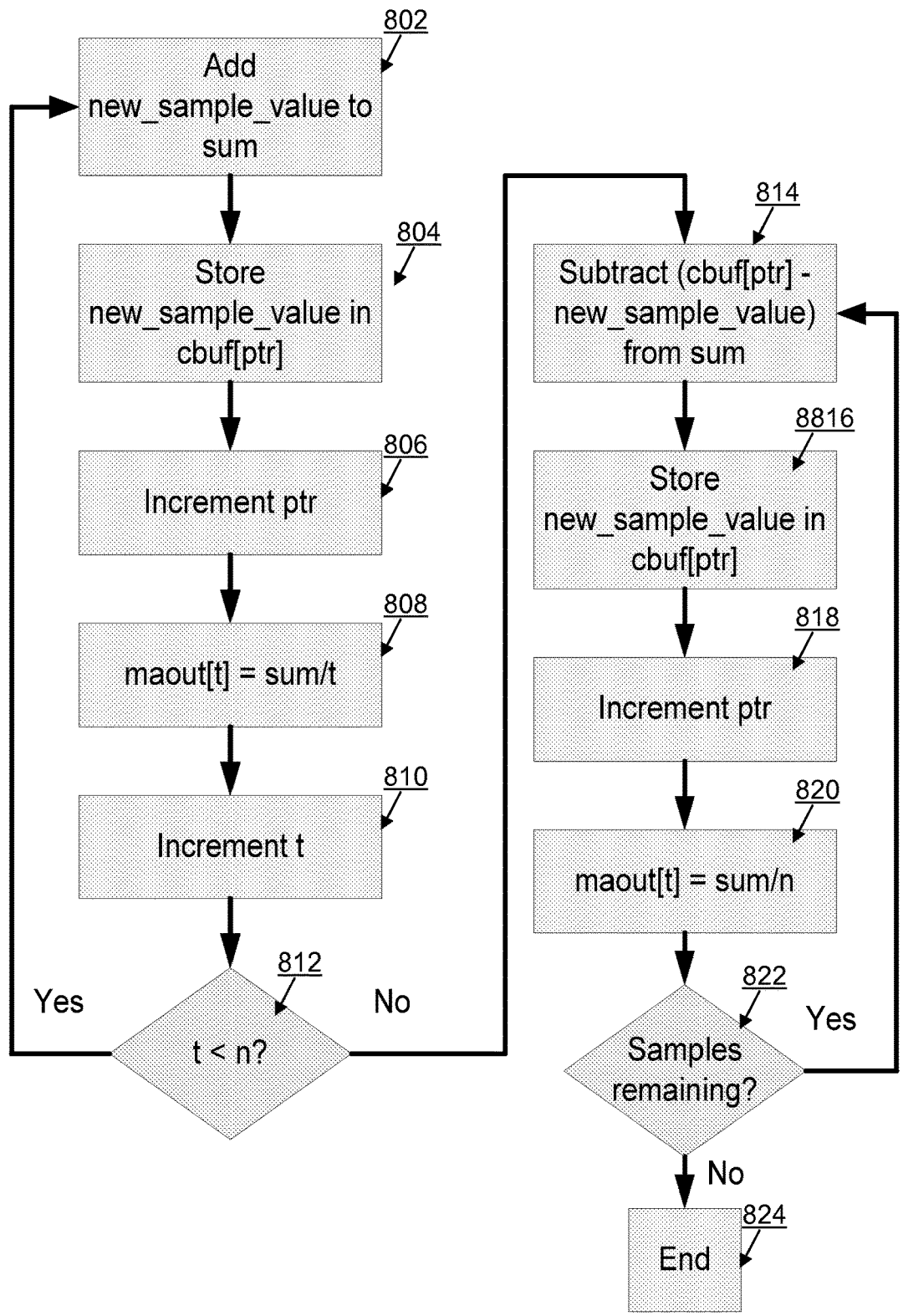
FIG. 8 is a flow diagram detailing an algorithm for obtaining a moving average of a signal according to the current subject matter.

The operation of each moving average filter will now be described with reference to FIGS. 7A-7C and 8. FIGS. 7A-7C depict an ECG waveform at three different points in time to illustrate the moving average filtering process which is described, in the flow diagram of FIG. 8. FIG. 8 depicts the steps of a filtering algorithm implemented by any of the moving average filters 508a-508c. Again, the operation of each filter is the same with the only difference being the cutoff frequency of each filter. Thus, while the following description will reference a single moving average filter, it should be understood that any of the moving average filters of the set of moving average filters 508 will be specifically programmed to execute the filtering algorithm of FIG. 8.

Referring now to FIG. 7A, an ECG waveform 702 derived from the preprocessed signal is shown. The filter generates a detection window 704 having a predetermined duration of k seconds. This is indicated in FIG. 7A as the k-second window. The moving average is taken over a moving average window 706 that includes a subset of points within the detection window beginning at the earliest point in time. This is shown in FIG. 7A as the n-second moving average window. An n-second moving average filter is applied to the ECG waveform on a point-by-point basis within the k-second window. Note that this can be done for any n<k where n=1/f, with f being the frequency of interest. The moving average moves one point at a time through the entire k-second window, producing a lowpass version of the signal. An exemplary moving average filter algorithm is shown in FIG. 8.

As can be seen in FIG. 8, a flow diagram detailing steps in the form of pseudocode is shown. For the psuedocode shown in FIG. 8, the following definitions apply:
n-sample circular buffer, cbuf
temporary variable to hold sum, sum
buffer to store the moving average, maout
pointer initialized to zeroth element of cbuf, ptr
the current sample value, new_sample_value
variable to store current time in samples, t In step 802, data representing a current sample (new_sample_value) is added to the temporary variable sum. In step 804, the data representing the current sample is stored in the n-sample circular buffer (cbuf) which is tied to the pointer initialized to the zeroth element of the circular buffer (ptr). The n-sample circular buffer has a size that corresponds to the moving average window 706 in FIG. 7 that comprises the n-second window. In step 806, the pointer (ptr) is incremented to the next element of the circular buffer (cbuf). In step 808, the moving average of the data samples stored in sum at time t is computed by dividing the data samples in sum by the value of current time in the samples t. he The current time stored in t is then incremented in step 810. In step 812, a query as to whether the value of time t is less than the value of n representing the length of the moving average window is made. If the result of the query in step 812 is positive, then steps 802-810 are repeated. The result of this repetition fills the buffer cbuf and computes the averages for the initial n samples of the moving average window (706 in FIG. 7). If the result of the query in step 812 is negative the algorithm proceeds to step 814 where the next new_sample_value is substracted from the values stored in the circular buffer cbuf[ptr] and that difference is subtracted from the values stored in sum. This clears the circular buffer to reinitialize it to calculate the moving average for a subsequent moving average window that begins when a current time is equal to the total length of the moving average window (t=n). In step 816, the values of the new current sample new_sample_value is stored in the circular buffer cbuf and the pointer value ptr is incremented in step 818 to the next point in time within the moving average window. The moving average maout at time t is computed by dividing the values stored in sum by the number of samples in the moving average window n in step 820. The algorithm then queries, in step 822, whether there are any additional samples incoming and if there are, the algorithm repeats steps 814-822. If the result of the query in step 822 is negative, then the algorithm ends in step 824.

Exemplary pseudocode described in FIG. 8 may be as follows:
For the first n samples, do the following:

```
sum += new_sample_value
cbuf[ptr] = new_sample_value
ptr++
maout[t] = sum/t
##This will fill the buffer and compute averages for the initial n samples.##
```

For all remaining samples, do the following:

sum-=$cubf[ptr]$-new_sample_value $cbuf[ptr]$=new_sample_value $ptr$++ maout[$t$]=sum/$n$

The above psuedocode is provided for purposes examples only and should not be considered as the only manner in which to determine the moving average.

Steps 802-812 of the algorithm in FIG. 8 are visually depicted in FIG. 7A. Thereafter, in FIG. 7B, the continual progression of the moving average window 706 is readily seen. In FIG. 7B, the moving average window has shifted to a later point in time. Thus, there is a successive determination of the moving average within the detection window 704 until such time that the moving average window 706 reaches a point in time where a current time equals k defining the duration of the detection window in seconds. This successive determination of the moving average for the samples in the signal are reflected in steps 814-822 in FIG. 8. Thereafter, the filter shifts the detection window by one of (a) k seconds (as shown in FIG. 7C) or (b) k/2 seconds which provides an overlapped region enabling recalculation of the moving average for certain points within the original detection window. The result of the moving average filter yields a vector representing a collection of the averages that approximates a LPF version of the signal with a cutoff of approximately $F_s/n$ Hz, where $F_s$ is the sampling frequency in Hertz.

Referring back to FIG. 5, the resulting data representing the moving averages calculated by each of the moving average filters in the set of moving average filters are output to the feature extraction module 510 which uses the various data to determine at least one feature associated with the signal being sensed and monitored by the device. As discussed above with respect to FIG. 2, the feature extraction module 510 executes a plurality of different feature calculation algorithms that use different input signals as the basis from which the respective feature is determined. The feature extraction module 510 is configured to execute algorithms that compute the following features which were determined to provide a sufficient level of specificity and sensitivity for determining the presence of artifacts in a signal. The features calculated by the extraction processor include at least one of:

Relative power in QRS band ($P_{5\text{-}15\ Hz}/P_{5\text{-}40\ Hz}$)
Relative power after HPF, cutoff=5 Hz ($P_{5\text{-}40\ Hz}/P_{0\text{-}40\ Hz}$)
Max value from raw signal
Sum of raw signal values
Max value-mm value
Samples >0.5 mV above baseline
Samples <0.5 mV below baseline
Max value of difference buffer
Sum of difference buffer values
Result of signal quality index calculation in U3 operator
Result of signal quality index calculation in difference buffer
Maximum value in U3 operator
Sum of values in U3 operator
Result of signal quality index calculation in U3 operator
Number of peaks as calculated by the HF artifact detector
Relative power in baseline $1-(P_{0\text{-}1\ Hz}/P_{0\text{-}40\ Hz})$
Flatline detection
Skewness and Kurtosis
Total energy in absolute second difference
Total energy in U3 operator
($P_{0\text{-}5\ Hz}/P_{15\text{-}40\ Hz}$)
($P_{0\text{-}5\ Hz}/P_{5\text{-}40\ Hz}$)
($P_{5\text{-}40\ Hz}/P_{0\text{-}40\ Hz}$)
($P_{10\text{-}40\ Hz}/P_{0\text{-}40\ Hz}$)
Total energy in raw signal buffer
Total energy in difference buffer
Total energy in first difference
Total energy in second difference
Standard deviation of samples in raw signal buffer
Standard deviation of samples in difference buffer
Standard deviation of signal after LPF, cutoff frequency=5 Hz
Standard deviation of signal after HPF, cutoff frequency=10 Hz The features described above that are italicized represent features that are conventionally calculated as part of ECG processing. Thus, the artifact detection algorithm according to the current subject matter includes a set of features that advantageously improve the specificity and sensitivity with which artifacts are detected while minimizing the computational complexity required to obtain the features on which this classification is based. For the non-italicized features, a discussion as to how these features may be calculated is provided hereinbelow.

A first feature calculated by the feature extraction module 510 is a value representing a relative power in the QRS band. This is obtained by dividing the power in the second bandpass signal (5-15 Hz) 608c which is output from the third moving average filter 508c in FIG. 6 by the power in the first bandpass signal 608b (5-40 Hz) which is obtained by subtracting the output of the second moving average filter 508b from the original full spectrum preprocessed signal. Another power-based feature calculated by the feature extraction module 510 is a relative power in the baseline which is obtained by dividing the power in the first filtered output signal 608a (0-1 Hz) by the power in the full spectrum preprocessed signal (0-40 Hz). The use of the moving average filter to obtain the inputs from which these power based features are determined advantageously enables the ECG monitoring device to generate the inputs used for calculating features and detecting the presence of artifacts in a signal in real-time. This holds true because power calculations obtained by filtering a signal in the time domain can yield an acceptable approximation of the power in the frequency domain without requiring the computational resources typically required to calculate power directly in the frequency domain. An exemplary algorithm for calculating the power based features discussed above is shown in FIG. 9. This algorithm will effectively calculate the relative power between any two input signals provided.

Figure 9:
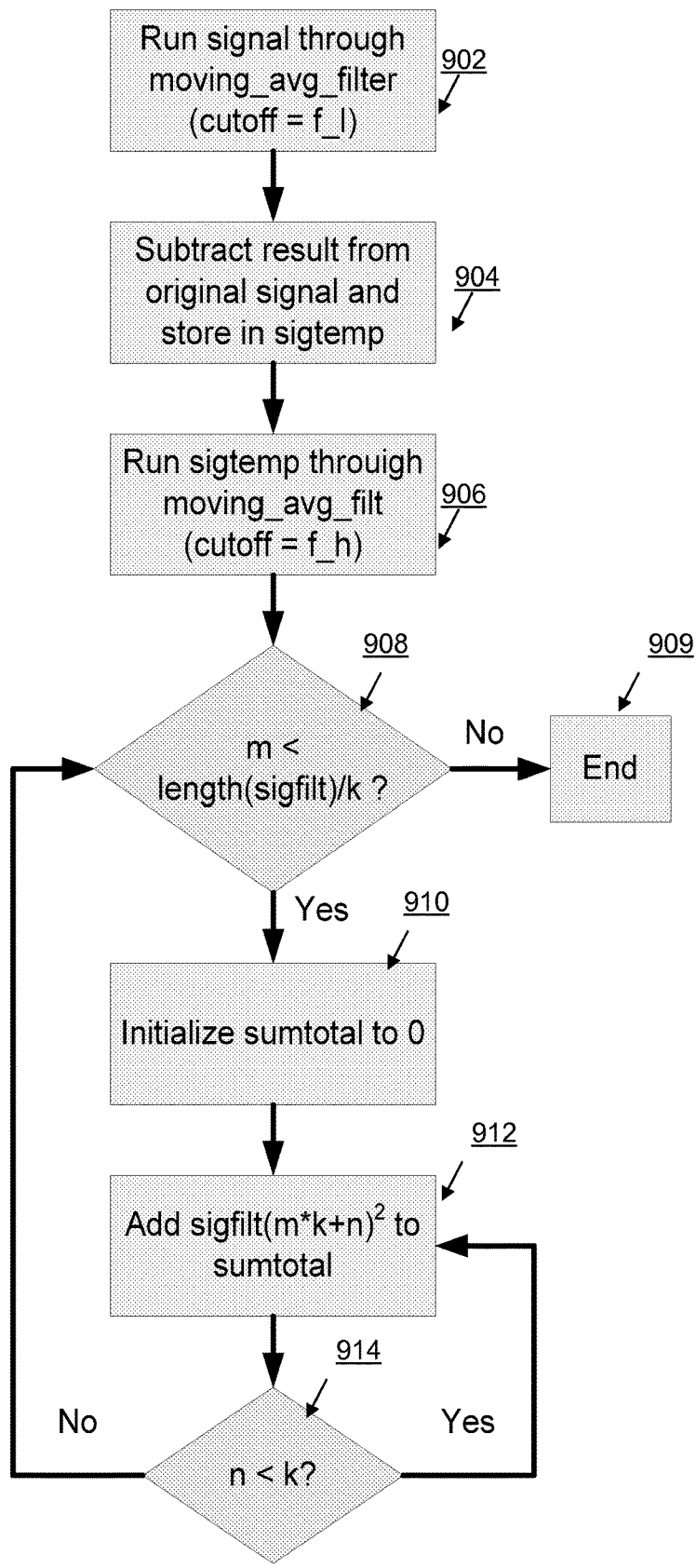
FIG. 9 is a flow diagram detailing an algorithm for calculating at least one power based feature associated with the signal being filtered by a moving average filter according to the current subject matter.

FIG. 9 provides an algorithm for calculating a relative power value between a lower limit $f_l$ and an upper limit $f_h$. In the algorithm of FIG. 9, the variables used therein are defined as follows:

Vector with ECG signal after prefiltering but before moving average filtering, signal
Vector to hold ECG signal after moving average filtering, sigfilt
Vector to hold intermediate filtered ECG signal, sigtemp
Integer to store low-frequency cutoff, f_l
Integer to store high-frequency cutoff, f_h
Integer to store window length, k
Loop counter integers, m and n In step 902, the preprocessed signal is filtered by a moving average filter having the lowest frequency cutoff of interest defining the lower bound of the bandpass signal (cutoff=$f_l$). In step 904, the resulting output moving average vector is subtracted from the original full spectrum preprocessed signal and stored in a vector which holds an intermediate filtered ECG signal (sigtemp). The intermediate filtered signal stored in sigtemp is further filtered, in step 906, through a moving average filter with a cutoff frequency $f_h$ representing the upper bound of the bandpass signal from which the power calculation is being made. The result of this bandpass filtering is stored in the vector sigfilt. After completion of steps 902-906, the algorithm, for each value stored in vector sigfilt, iterates through the following loop comprising steps 908-914. The loop includes counter integers m associated with the loop iteration and n representing the sample of data stored in the vector sigfilt. In step 908 a query is made to determine whether a current integer m is less than a length of vector in sigfilt divided by a length of the detection window k. If this is false, then the algorithm ends in step 909. If the result of the query of step 908 is true, the sub-loop relating to the data samples in vector sigfilt is initiated. Thus, in step 910, a variable sumtotal is initialized at zero. In step 912, the sum of the squares of sigfilt for sample n is added to the variable sumtotal. In step 914, the algorithm determines if the sample being looped has a value less than a value of k defining the length of the detection window. If this is true, the algorithm increments the counter n for the next sample from the vector sigfilt, and repeats steps 912 to modify sumtotal as above. If the result of the query in step 914 is negative, the algorithm repeats the query in step 908 to reinitialize a further loop. Once sumtotal has been appended to include all samples in the vector, the value of sumtotal may be initialized as a variable representing the power (pwr) of the bandpass signal obtained from the moving average filtering discussed above.

Exemplary pseudocode for implementing the algorithm described in FIG. 9 is as follows. Initially, the original signal is filtered using, moving average filters (see FIGS. 6-8) such that the frequency content of the output is substantially limited to the range ($f_l$, $f_h$) inclusive. Assuming a subfunction moving_avg_filter (the instructions for implementing this subfunction being found in FIG. 8), it can be described as sigtemp=signal−moving_avg_filter(signal,$f\_l$)

sigfilt=moving_avg_filter(sigtemp,$f\_h$)

Once this is determined, the algorithm iterates through the following loop:

```
for (m = 0, m < length(signal)/k, m++)
{
    sumtotal = 0
    for (n = 1, n < k, n++)
    {
        sumtotal = sumtotal + sigfilt(m*k+n)*sigfilt(m*k+n)
    }
    pwr(m) = sumtotal
}
```

The result is the power calculation for each m is equal to the value stored in sumtotal. In another embodiment, if the relative power in different frequency bands is the subject of interest (rather than the power calculations themselves) the sum of the squares of sigfilt can be replaced by the sum of the absolute values of sigfilt for computational simplicity.

The resulting power features calculated in accordance with the algorithm in FIG. 9 may then be provided as inputs to the pattern classification algorithm executed by the artifact detection classifier 512 (or classification processor 212 in FIG. 2). However, prior to discussing the use of these features to compute a classifier used to identify artifacts, it is important to refer back to the other components of the ECG monitoring device 502 that generate the remaining features of the set of features discussed above.

The ECG monitoring device 502 also includes a differentiator 514 (differentiation processor 214 in FIG. 2). The differentiator 514 determines a first and second difference (or derivative) between successive samples in the detection window. The first derivative of f(x) is defined as the slope of a line tangent to f(x) at sample x. Thus, the first derivative can be approximated by f(x+1)−f(x), assuming that the samples are reasonably close together. This result is known as the first difference. We can also estimate the second derivative from estimating the derivative of the first difference via the formula f(x+2)−2f(x+1)+f(x). Data representing the first difference and the second difference is stored in the difference buffer of the differentiator 514. The data in the difference buffer is provided to the feature extraction module 510 and is able to calculate features using the difference data stored therein. In the feature set used by the ECG monitoring device of FIG. 5, the feature extraction module 510 calculates a feature representing a maximum value of the difference buffer as well as a feature representing a sum of the difference buffer values. The difference buffer values are calculated by adding the first and second differences together. Once this signal is computed, a certain-sized window is taken, and the maximum value in that window is found, as well as the sum of all the difference buffer samples in that window. These features are also provided to the artifact detection classifier 512 for use in determining a classifier to identify the presence of the artifacts as will be discussed below.

Additionally, the feature extraction module 510 also receives, as an input, the preprocessed full spectrum pre-filtered ECG signal. From this pre-filtered ECG signal, the feature extraction module 510 is able to calculate additional features of the feature set described above. A first feature determined from the pre-filtered ECG signal is a maximum value of the pre-filtered ECG signal within the detection window. A second feature determined from the pre-filtered ECG signal is a sum of the values of the pre-filtered signal within the detection window. A third feature determined from the pre-filtered ECG signal is a difference between a maximum value within the detection window and a minimum value within the detection window. A fourth feature determined from the pre-filtered ECG signal is a number of samples having a predetermined amplitude (e.g. 0.5 mV) above a baseline value. A fifth feature determined from the pre-filtered ECG signal is a number of samples having a predetermined amplitude (e.g. 0.5 mV) below a baseline value. At least one of these features determined from the pre-filtered ECG signal are similarly provided to the artifact detection classifier 512 along with the power based features derived from a moving average filtering process and the difference based features determined by obtaining the first and second difference of the pre-filtered ECG signal.

In another embodiment, the feature extraction module 510 may also determine features related to at least one of (a) a skewness value of the signal within the detection window; (b) a kurtosis value of the signal within the detection window; (c) an amount of energy in the U3 operator of the signal; and (d) the detection of a flatline in the detection window. Skewness is a measure of the asymmetry of the data around the sample mean. If skewness is negative, the data are spread out more to the left of the mean than to the right. If skewness is positive, the data are spread out more to the right. The skewness of the normal distribution (or any perfectly symmetric distribution) is zero.

The skewness of a distribution is defined as $$s = \frac{E(x-\mu)^3}{\sigma^3}$$

where μ is the mean of x, σ is the standard deviation of x, and E(t) represents the expected value of the quantity t.skewness computes a sample version of this population value. Kurtosis is a measure of how outlier-prone a distribution is. The kurtosis of the normal distribution is 3. Distributions that are more outlier-prone than the normal distribution have kurtosis greater than 3; distributions that are less outlier-prone have kurtosis less than 3.

The kurtosis of a distribution is defined as $$k = \frac{E(x-\mu)^4}{\sigma^4}$$

where μ is the mean of x, σ is the standard deviation of x, and E(t) represents the expected value of the quantity t.kurtosis computes a sample version of this population value. The energy is calculated in the usual way, as the sum of the squares of the signal values (i.e., $E=\text{sum}(x[n]^2)$ for all n). In general, flatness is determined by checking whether the absolute value of the difference between consecutive signals is below some very low threshold. If the difference is very small over an extended period of time (on the order of seconds), this could indicate (for example) a problem with the electrode connection.

Once all the features have been determined by the feature extraction module 510, they are provided as respective inputs to the artifact detection classifier 512. In the embodiment discussed above, there are nine features determined by the feature extraction module 510 and each are used by the artifact detection classifier 512 to determine a classifier which may then be used to identify whether the signal within the detection window includes an artifact. As discussed above, the artifact detection classifier 512 executes a dynamic neural network that has been fully trained. It is due to this complete training that the feature extraction module 510 is configured to calculate the respective features. During the neural network training process, a number of hidden nodes are selected for use in processing the nine features input thereto. It is desirable to have enough hidden nodes that the specificity and sensitivity of the classifier being determined is above a predetermined threshold but, as the number of hidden nodes included in the dynamic neural network increase, so too does the computational complexity. In one embodiment, the result of the training indicates that a dynamic neural network to be implemented by the artifact detection classifier may include at least 13 hidden nodes.

While training a dynamic neural network, a number of hidden nodes are selected and data representing the set of features from which the classifier is to be determined are provided as inputs. The dynamic neural network selects a weight to be applied to each node and the input data (e.g. feature data) is propagated through the hidden nodes of the network and the weights of each hidden node are applied to the respective features. After propagation, the dynamic neural network outputs a classifier. The classifier output after each training run is then validated with a set of validation data and the dynamic neural network learns from any discrepancy between its output and the actual element sought. In this case, the classifier output is intended to indicate the presence or absence of an artifact and the dynamic neural network will determine how close the classifier output was to the actual event being classified. The dynamic neural network then goes back and modifies the weights associated with different hidden nodes to try to improve the classifier being output. Further training data is applied to the dynamic neural network after updating of the hidden node weights, and the process is repeated until the dynamic neural network has learned and discovered the correct weights to be applied to each node in order to produce a classifier that is consistently above a predetermined quality threshold indicating that the dynamic neural network will be able to successfully determine the classifier and that the classifier will be sufficiently sensitive and specific in indicating that the event (e.g. artifact) is present.

It is this resulting structure of the trained dynamic neural network that is implemented and executed by the artifact detection classifier 512. Thus, artifact detection classifier 512 takes a predetermined number of inputs and passes them through a predetermined number of hidden nodes, each having its own weight that the dynamic neural network determined itself during training. As each input data is propagated through the hidden nodes using the weights associated therewith, a classifier value is calculated. The classifier value is compared with a threshold value indicative of the presence of an artifact. If the classifier value exceeds the threshold value, the artifact detection classifier flags the section of the preprocessed signal as including an artifact. The parameter processor (204 in FIG. 2) can detect the flags and automatically suspends parameter processing function for the duration indicated in the flag thereby minimizing the use of signal data having a poor quality. By minimizing the use of signals having poor quality, the patient monitoring device will generate fewer false alarms while improving the determination of respective patient parameters because the portions of the signals which are not flagged are ostensibly higher quality enabling the parameter processor to generate more accurate patient parameters.

Figure 10:
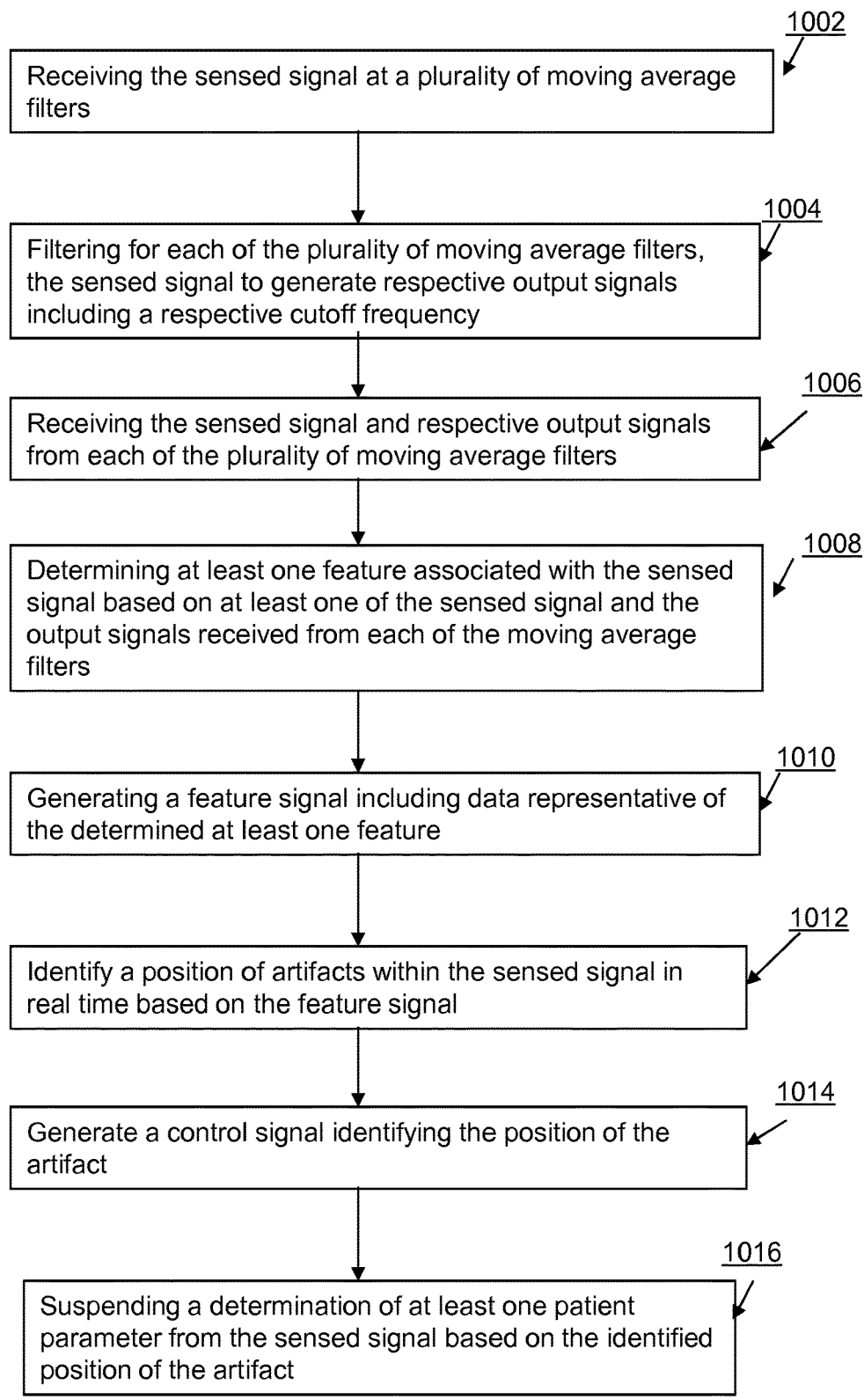
FIG. 10 is a flow diagram detailing an algorithm for detecting artifacts in a signal according to the current subject matter.

FIG. 10 is a flow diagram detailing an exemplary algorithm executed by a patient monitoring device such as described in either FIG. 2 or 5 that advantageously, and in real time, identifies artifacts in a signal sensed by at least one sensor coupled to a patient. In step 1002, the sensed signal is received at a plurality of moving average filters and, in step 1004, for each of the plurality of moving average filters, the sensed signal is filtered signal to generate respective output signals including a respective cutoff frequency. In one embodiment, for each of the plurality of moving average filters the output signal is generated for a predetermined number of samples within a window of time having a predetermined length.

In another embodiment, the output signals generated by the plurality of moving average filters include first and second bandpass signals. In this embodiment, a summer combines the sensed signal and an output of one of the plurality of moving average filters to generate a first bandpass signal having a predetermined frequency range. Additionally, at a second of the plurality of the moving average filters, the first bandpass signal is received from the summer to generate a second bandpass signal having a second predetermined frequency range.

At step 1006, an extraction processor receives the sensed signal and respective output signals from each of the plurality of moving average filters and, in step 1008, determines at least one feature associated with the sensed signal based on at least one of the sensed signal and the output signals received from each of the moving average filters.

In one embodiment the output signals received by the extraction processor include the first and second bandpass signals as discussed above and the step determining at least one feature includes determining a relative power within a predetermined frequency range by dividing the power in the second bandpass signal by the power in the first bandpass signal in real time. Additionally, or alternatively, the activity of determining the at least one feature includes determining a relative power in a baseline by:

1−(S1/S2)

wherein, S1 is the power in an output signal of a first of the plurality of moving average filters and S2 is the power in the sensed signal.

A feature signal including data representative of the determined at least one feature is generated in step 1010. In one embodiment, the extraction processor generates the feature signal based on the sensed signal and the feature signal includes data representative of at least one of (a) a skewness value of the signal within the detection window; (b) a kurtosis value of the signal within the detection window; (c) an amount of energy in the U3 operator of the signal; and (d) the detection of a flatline in the detection window. In another embodiment, the extraction processor generates the feature signal based on the output signals of the moving average filters and the feature signal including data representative of at least one of (a) relative power in a first predetermined frequency band; and (b) a relative power in a baseline of the sensed signal. In a further embodiment, the feature signal is generated based on the sensed signal and the respective output signals of the plurality of moving average filters.

In another embodiment, the sensed signal is received at a at a differentiation processor coupled to the extraction processor which generates a differentiation signal based on data representative of a first difference between successive samples of the sensed signal and data representative of a second difference between successive samples of the first difference. In this embodiment, the extraction processor generates the feature signal based on at least one of the sensed signal, the output signals of the moving average filters and the differentiation signal.

In step 1012, a classification processor identifies a temporal position of one or more artifacts within the sensed signal in real time based on the feature signal. In step 1014, the classification processor generates a control signal identifying the position of the artifact. In one embodiment, the step of generating a control signal that identifies the position of artifacts includes determining a classifier value from the feature signal using a dynamic neural network and identifying the position of the artifacts when the determined classifier value one of exceeds or falls below a threshold value.

In step 1016, a patient parameter processor receives the control signal and suspends a determination of at least one patient parameter from the sensed signal based on the identified position of the artifact.

Although the current subject matter has been described in terms of exemplary embodiments, it is not limited thereto. Rather, the appended claims should be construed broadly to include other variants and embodiments of the current subject matter which may be made by those skilled in the art without departing from the scope and range of equivalents of the current subject matter. This disclosure is intended to cover any adaptations or variations of the embodiments discussed herein.

What is claimed is:

1. A patient monitoring apparatus comprising:
a plurality of moving average filters, each of said plurality of filters receives a signal sensed from a patient and generates an output signal, each of said plurality of filters having a respective cutoff frequency;
an extraction processor coupled to receive the sensed signal and output signals from each of the plurality of moving average filters, said extraction processor determines at least one feature associated with the sensed signal based on at least one of the sensed signal and the output signals received from each of the moving average filters and generates a feature signal including data representative of the determined at least one feature; and
a classification processor that identifies a temporal position of one or more artifacts within the sensed signal based on the feature signal and generates a control signal identifying the temporal position of the artifact, wherein a summer combines the sensed signal and an output of a first of the plurality of moving average filters to generate a first bandpass signal having a predetermined frequency range,
a second of the plurality of the moving average filters receives the first bandpass signal from the summer to generate a second bandpass signal having a second predetermined frequency range, and
the at least one feature determined by the extraction processor includes a relative power within a predetermined frequency range, the relative power being determined by dividing a power in the second bandpass signal by a power in the first bandpass signal.

2. The apparatus according to claim 1, further comprising:
a patient parameter processor that suspends a determination of at least one patient parameter from the sensed signal based on the identified temporal position of the one or more artifacts.

3. The apparatus according to claim 1, wherein
each of the plurality of moving average filters generates the output signal for a predetermined number of samples within a window of time having a predetermined length.

4. The apparatus according to claim 1, wherein the dividing of the power in the second bandpass signal by the power in the first bandpass signal occurs in real time.

5. The apparatus according to claim 1, wherein
the at least one feature includes a relative power in a baseline signal, the relative power in a baseline signal being determined by:

$$1-(S1/S2)$$

wherein, S1 is a power in an output signal of the first of the plurality of moving average filters and S2 is a power in the sensed signal.

6. The apparatus according to claim 1, wherein
the extraction processor generates the feature signal based on the sensed signal, the feature signal including data representative of at least one of (a) a skewness value of a signal within a detection window; (b) a kurtosis value of the signal within the detection window; (c) an amount of energy in a U3 operator of the signal; and (d) a flatline in the detection window.

7. The apparatus according to claim 1, wherein
the extraction processor generates the feature signal based on the output signals of the moving average filters, the feature signal including data representative of at least one of (a) relative power in a first predetermined frequency band and (b) relative power in a baseline of the sensed signal.

8. The apparatus according to claim 1, further comprising
a differentiation processor coupled to the extraction processor, the differentiation processor receives the sensed signal and generates a differentiation signal based on data representative of a first difference between successive samples of the sensed signal and data representative of a second difference between successive samples of the first difference; wherein
the extraction processor generates the feature signal based on at least one of the sensed signal, the output signals of the moving average filters and the differentiation signal.

9. The apparatus according to claim 1, wherein
the classification processor is a dynamic neural network that determines a classifier value from the feature signal and identifies the temporal position of the one or more artifacts when the determined classifier value exceeds or falls below a threshold value.

10. The apparatus according to claim 1, wherein
the classification processor identifies the temporal position of the one or more artifacts within the sensed signal in real time.

11. A method of detecting artifacts in a signal sensed by at least one sensor connected to a patient, the method comprising:
receiving the sensed signal at a plurality of moving average filters;
for each of the plurality of moving average filters, filtering the received sensed signal to generate respective output signals including a respective cutoff frequency;
receiving, at an extraction processor, the sensed signal and respective output signals from each of the plurality of moving average filters;
determining, by the extraction processor, at least one feature associated with the sensed signal based on at least one of the sensed signal and the output signals received from each of the moving average filters;
generating a feature signal including data representative of the determined at least one feature; and
identifying, by a classification processor, a temporal position of one or more artifacts within the sensed signal based on the feature signal and generating a control signal identifying the position of the one or more artifacts,
wherein the method further comprises
combining, by a summer, the sensed signal and an output of a first of the plurality of moving average filters to generate a first bandpass signal having a predetermined frequency range,
receiving, at a second of the plurality of the moving average filters, the first bandpass signal from the summer, and
generating a second bandpass signal having a second predetermined frequency range, and
wherein, in the determining by the extraction processor, the at least one feature includes a relative power within a predetermined frequency range, the relative power being determined by dividing a power in the second bandpass signal by a power in the first bandpass signal.

12. The method according to claim 11, further comprising:
suspending a determination by a patient parameter processor of at least one patient parameter from the sensed signal based on the identified position of the one or more artifacts.

13. The method according to claim 11, further comprising for each of the plurality of moving average filters, generating the output signal for a predetermined number of samples within a window of time having a predetermined length.

14. The method according to claim 11, wherein the dividing of the power in the second bandpass signal by the power in the first bandpass signal occurs in real time.

15. The method according to claim 11, wherein the determining of the at least one feature includes
determining a relative power in a baseline signal by:

$$1-(S1/S2)$$

wherein, S1 is a power in an output signal of the first of the plurality of moving average filters and S2 is a power in the sensed signal.

16. The method according to claim 11, further comprising generating, by the extraction processor, the feature signal based on the sensed signal, the feature signal including data representative of at least one of (a) a skewness value of a signal within a detection window; (b) a kurtosis value of the signal within the detection window; (c) an amount of energy in a U3 operator of the signal; and (d) a flatline in the detection window.

17. The method according to claim 11, wherein
the extraction processor generates the feature signal based on the output signals of the moving average filters, the feature signal including data representative of at least one of (a) relative power in a first predetermined frequency band and (b) relative power in a baseline of the sensed signal.

18. The method according to claim 11, further comprising
receiving the sensed signal at a differentiation processor coupled to the extraction processor;
generating a differentiation signal based on data representative of a first difference between successive samples of the sensed signal and data representative of a second difference between successive samples of the first difference; and
generating, by the extraction processor, the feature signal based on at least one of the sensed signal, the output signals of the moving average filters and the differentiation signal.

19. The method according to claim 11, wherein the activity of identifying further includes
determining a classifier value from the feature signal using a dynamic neural network; and
identifying the temporal position of the one or more artifacts when the determined classifier value exceeds or falls below a threshold value.

20. The method according to claim 11, wherein identifying the temporal position of the one or more artifacts within the sensed signal is in real time.

21. A system comprising at least one data processor; and memory storing instructions which, when executed by the at least one data processor, causes the at least one data processor to perform operations comprising:
receiving a sensed signal at a plurality of moving average filters, the sensed signal being generated by at least one sensor connected to a patient;
for each of the plurality of moving average filters, filtering the received sensed signal to generate respective output signals including a respective cutoff frequency;
receiving, at an extraction processor, the sensed signal and respective output signals from each of the plurality of moving average filters;
determining, by the extraction processor, at least one feature associated with the sensed signal based on at least one of the sensed signal and the output signals received from each of the moving average filters;
generating a feature signal including data representative of the determined at least one feature; and
identifying, by a classification processor, a temporal position of one or more artifacts within the sensed signal based on the feature signal and generating a control signal identifying the position of the one or more artifacts,
wherein the operations further comprise
combining, by a summer, the sensed signal and an output of a first of the plurality of moving average filters to generate a first bandpass signal having a predetermined frequency range,
receiving, at a second of the plurality of the moving average filters, the first bandpass signal from the summer, and
generating a second bandpass signal having a second predetermined frequency range, and wherein, in the determining by the extraction processor, the at least one feature includes a relative power within a predetermined frequency range, the relative power being determined by dividing a power in the second bandpass signal by a power in the first bandpass signal.

* * * * *